United States Patent [19]

Schlein

[11] Patent Number: 4,905,374
[45] Date of Patent: Mar. 6, 1990

[54] MODULAR HAND TOOL SYSTEM

[76] Inventor: Allen P. Schlein, 107 Curtis Ter., Fairfield, Conn. 06432

[21] Appl. No.: 365,807

[22] Filed: Jun. 14, 1989

[51] Int. Cl.⁴ .................. B26B 3/00; B26B 11/00; B25G 1/00; B25G 3/02
[52] U.S. Cl. .................. 30/299; 30/164.9; 81/177.1; 16/114 R; 7/158
[58] Field of Search .......... 30/152, 172, 173, 197, 30/226, 279, 287, 299, 332, 337, 147, 122; 81/177.1, 489; 7/158; 16/110 R, 114 R, DIG. 41, DIG. 74

[56] References Cited

U.S. PATENT DOCUMENTS

| 3,173,317 | 3/1965 | Neff | 81/177.1 |
| 3,760,438 | 9/1973 | White | 7/158 |
| 3,921,288 | 11/1975 | Clemens, Jr. | 30/299 |
| 4,466,152 | 8/1984 | Moss et al. | 16/114 R |
| 4,829,976 | 5/1989 | Pourtau et al. | 30/164.9 |

Primary Examiner—Douglas D. Watts
Assistant Examiner—Paul M. Heyrana
Attorney, Agent, or Firm—Spencer E. Olson

[57] ABSTRACT

A modular hand tool system in which a tool piece is detachably secured to a handle has an elongated planar handle having a centrally located rectangularly-shaped cutout extending inwardly from one end. The tool piece, which may take a variety of forms, has a shank portion of substantially the same shape and size as the cutout and is received therein with a tight sliding fit. The tool piece is detachably secured in the cutout by a screw mechanism including an elongated rod supported within and anchored at one end to the handle at a point displaced from the tool piece and which at its other end threadably engages a threaded opening formed in the shank portion of the tool piece.

6 Claims, 2 Drawing Sheets

MODULAR HAND TOOL SYSTEM

BACKGROUND OF THE INVENTION

This invention relates generally to tools and instruments of a type and size to be hand-manipulable and, more particularly, to a modular system of hand tools consisting of one or more tool pieces which require reconditioning from time to time and a toolpiece holder or handle to which the tool piece is detachably secured.

Even though machine shops usually employ skilled personnel to sharpen tools and instruments, it is becoming more and more commonplace to use modular tool systems to reduce costs and better insure the availability of properly sharpened tools. Basically, under the modular concept a machine shop, for example, maintains a supply of tool pieces with properly sharpened edges which can be be releasably fixed on a tool holder so as to be easily removed when it becomes dull or damaged and replaced by a sharp one. Thus, a machining operation is interrupted for only the time required to remove a chipped or dull tool and replace it with another taken from a supply kept in optimum condition by an expert hired for the purpose.

A somewhat analogous situation exists in the field of orthopaedic surgery in that skilled services are available for sharpening surgical tools, but the case is rare that the sharpening service is on the hospital premises. Instead, the people providing such services offer to call at the hospital on a regular schedule, say, every month or two, to pick up the tools needing sharpening, but unless the volume of work is significant experience has shown they will not show up. Moreover, although such sharpening services can sharpen and return tools with a relatively short turnaround time, because the surgeon never knows whether he is going to need a particular tool an hour later, two hours later or maybe not until next week, there is a tendency on the part of hospital staff to send instruments out for sharpening only if they are badly damaged. While many hospitals designate in-house personnel to sharpen surgical instruments instead of using outside sharpening services, more often than not such personnel lack sufficient training to be truly expert in the techniques necessary to insure the finest tooling. This long-recognized problem is exacerbated by the recent adoption and growing use of the technique of coating hardened stainless steel surgical cutting instruments to increase the Rockwell hardness and strength of the cutting tip. All of the cutting instruments used in orthopaedics are made of stainless steel because it does not oxidize when sterilized, the cutting edges of which are usually made of 440C stainless which has a hardness between about 55 and 60 on the Rockwell C scale, which is as much as 15 points lower than that of non-stainless tool steels, but which cannot be used in orthopaedic surgery because they would oxidize with sterilization. As a consequence, various coatings, such as titanium nitrate, have been developed which when applied over the hardened 440C stainless steel significantly increases the Rockwell hardness and strength of the cutting tip.

Although such coatings increase the cutting strength of the tip, the sharpened edges do nonetheless become dulled and sometimes chipped with extensive use. Any attempt to sharpen such tips with an abrasive wheel or stone immediately destroys the coating, which is only three-tenthousandth of an inch thick, thereby, in effect, destroying the tool piece. In order that the benefits of coating the cutting edge of stainless steel tool pieces, despite of problem of restoring the edge when it becomes dulled has led to the development of modular techniques in the manufacture of cutting implements utilized in orthopaedics. These techniques, which may be equally applicable and useful in the fabrication of wood carving and stone carving tools, for example, consist essentially of making a relatively small tool piece of hardened stainless steel and coating its sharpened edge to increase the strength and hardness, and then detachably securing the tool piece to a suitable handle by which the tool piece can be manipulated. In this way, when a surgeon first notices that the cutting edge of a tool piece he is using or plans to use is damaged, he can simply remove and dispose of the damaged tool piece, get a replacement tip from a supply cabinet, sterilize it, and attach it to the handle without delaying the surgical procedure.

The construction of currently available modular orthopaedic tools of which applicant is aware, makes tool piece replacement inconvenient and time-consuming, due to the fact that the tool piece is secured to a handle with set-screws and/or bolts which require some form of tool for loosening and re-tightening. Moreover, such attaching means interrupt the contour of the working end of the tool which desirably is smooth and without protuberances or depressions of any kind.

Accordingly, it is a primary object of the present invention to provide an improved modular hand tool system.

Another, more specific, object of the invention is to provide a modular hand tool system especially useful in orthopaedics which includes a multiplicity of cutting tools such as chisels, gouges, osteotomes, and the like, each adapted to be releasably secured to a handle with a finger-operated screw mechanism contained in the handle.

SUMMARY OF THE INVENTION

Briefly, the modular hand tool system according to the invention consists of only four parts: an elongated planar handle formed of a sterilizable material, a tool piece having a sharpened edge, an elongated rod supported in an axial bore formed in the handle, one end of which threadably engages a threaded opening in the tool piece, and a humbwheel secured to the other end of the rod which engages an opening through the handle and anchors the rod to the handle. The tool piece and the handle have substantially the same width and thickness, and one end of the handle has a centrally located contoured cutout in which a similarly dimensioned and contoured shank formed on the tool piece is received. Rotation of the thumbwheel in one direction secures the tool piece to the handle, and rotation in the opposite direction pushes the shank of the tool piece out of the contoured cutout to the point at which the threaded rod becomes disengaged and the tool piece can be removed with the fingers.

Other objects, features and advantages of the invention, and a better understanding of its construction and operation, will be had from the following detailed description, taken in conjunction with the accompanying drawings.

DESCRIPTION OF THE PREFERRED EMBODIMENTS

Figure 1:
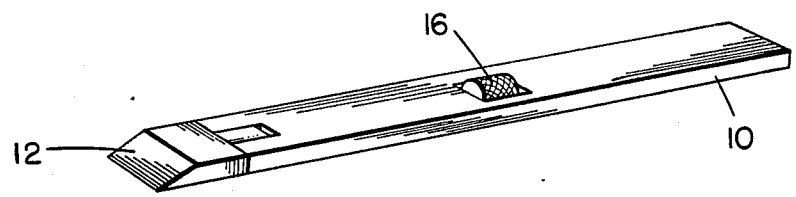
FIG. 1 is a perspective view of the modular tool system constructed according to the invention.

Referring to the drawings, the modular tool system according to the invention comprises an elongated handle member 10, preferably planar in shape and made of a sterilizable high impact material such as aircraft aluminum having a hard black coating, stainless steel or a high impact plastics material, a tool piece 12 detachably secured to one end of the handle, an elongated rod 14 threaded at both ends, and a knurled thumb wheel 16 threadably engaging one end of rod 14 and adapted to be secured at an adjusted position therealong by fastening means such as a set screw 18. Typically, the handle is about 8 inches long and of uniform width and thickness throughout its length. By way of example, the handle member may be ¼ inch thick and one inch wide.

Figure 2:
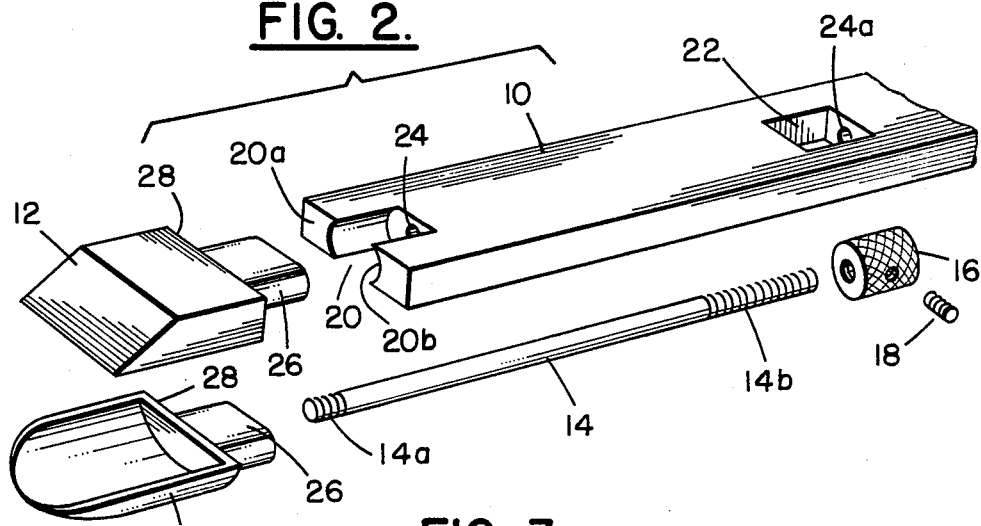
FIG. 2 is a fragmentary exploded perspective view of the tool system and showing two types of tool piece.
Figure 3:
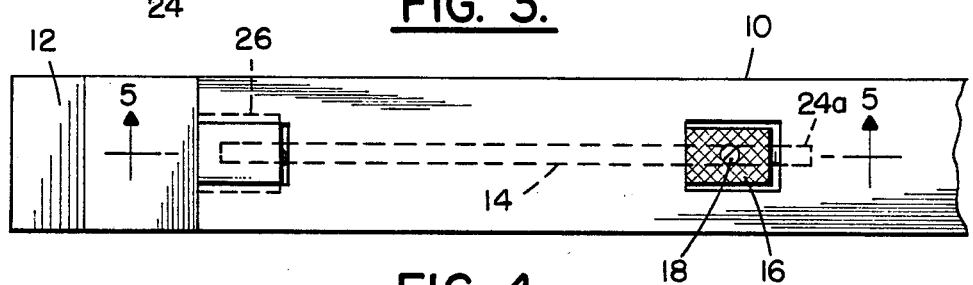
FIG. 3 is a fragmentary plan view of the tool system.
Figure 4:
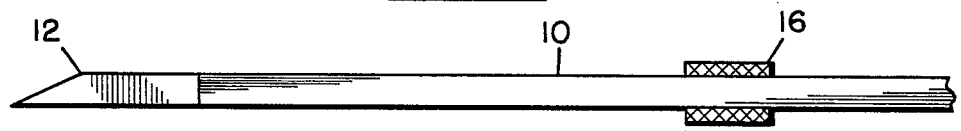
FIG. 4 is a fragmentary elevation view of the tool system.
Figure 5:
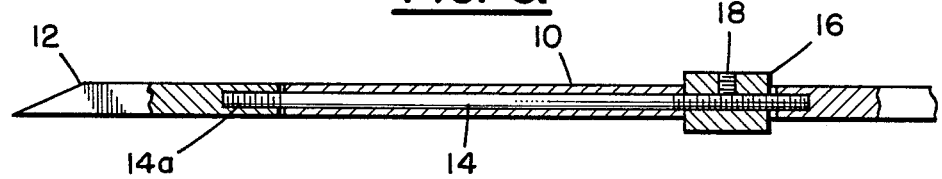
FIG. 5 is a fragmentary, elevation cross-section view taken along line 5—5 in FIG. 3.
Figure 6:
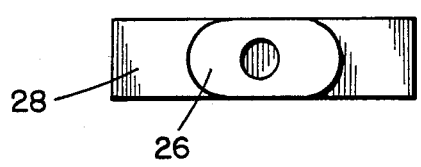
FIG. 6 is an elevation view of the right-hand end of the tool piece, as viewed in FIG. 2.
Figure 7:
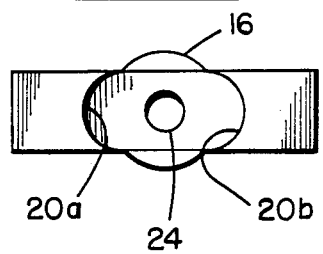
FIG. 7 is an elevation view of the left-hand end of the handle as viewed in FIG. 2.

As best seen in FIG. 2, at one end the handle member 10 has a first cutout 20 extending therethrough between its major surfaces, equidistant from the side edges, and extending longitudinally inward a predetermined distance, typically ½ inch. The longitudinally extending side surfaces 20a and 20b of the cutout have a simple curved contour, essentially a semicircular arc having a diameter substantially equal to the thickness of the handle, a shape easily formed with an end mill. Spaced inwardly from the first cutout by a distance substantially equal to the length of rod 14, typically about four inches so as to not interfere with the manipulation and use of the cutting edge of the tool piece, a second rectangularly-shaped cutout 22 extends through the handle and straddles the central longitudinal axis of the handle member equidistant from the side edges. An axial bore 24 having a diameter slightly larger than the diameter of rod 14 extends from the first cutout 20 to and across the second cutout 22 receives and supports the rod 14 for rotation therein.

The tool piece 12, which may be in the form of a chisel (shown in all of the figures) or of a gouge 24 (shown in FIG. 2 only), or any of the many other types of cutting tools used in orthopaedics, has substantially the same width and thickness as the handle 10 and at the end thereof opposite the cutting edge has a transverse surface to which a shank 26 is integrally joined. The shank portion 26, which in this example may be ½ inch long, ½ inch wide, and 3/16 inch thick, is positioned equidistant from the side edges of surface 28. The shank portion has curved side edges that match the curvature of the edges 20a and 20b of cutout 20, a curvature readily machinable with a rounding mill. The shank portion 26 is dimensioned to be received in the contoured cutout 20 with a tight sliding fit and when bottomed therein the transverse surface 28 firmly abuts the spaced apart end surfaces of the handle. The matching contours of the shank and cutout, although simple in shape, prevent relative rotation between the tool piece and handle, even when the tool piece is subjected to twisting in use, and are much less costly to machine than the complex dovetail mechanism used in some currently available modular tool systems.

The tool piece 12 and handle member 10 are maintained in assembled relationship by the elongated rod 14, supported within axial bore 24 and anchored at its inner end by knurled thumbwheel 16. During assembly, with the thumbwheel 16 held in position in opening 22, the rod 14 is inserted from the outer end of the bore 24 and threaded into the thumbwheel 16 by an amount such that when the thumbwheel abuts the edge of cutout 22 the free end projects from the bottom of cutout 20 by the length of the threaded portion 14a, typically about ¼ inch. The threaded portion 14b is sufficiently long to extend through thumbwheel 16 and across cutout 22 to be engaged in an extension 24a of the axial bore. Thumbwheel 16 is maintained at its adjusted position along the threaded portion 14b by a set screw 18 or equivalent securing means. With the rod 14 in place, the contoured shank portion of the tool piece 12 is inserted into the contoured cutout 20 in the handle far enough for the initial thread of threaded portion 14a to engage the threaded axial opening 26a in the shank portion, and then upon rotation of the rod 14 by finger manipulation of the thumbwheel is drawn the rest of the way into the cutout 20 at which the transverse surface 28 firmly engages the end surfaces of the handle so as to firmly and rigidly lock the tool piece and handle together. When it becomes necessary to replace the tool piece with a new one, the thumbwheel is simply rotated in the opposite direction, causing the threaded portion 14a to push the shank portion from the cutout by a distance equal to the length of the threaded portion 14a at which point it becomes disengaged and can be withdrawn the rest of the way by the fingers. Thus, it is seen that the tool piece and handle can be easily and conveniently assembled and disassembled with a screw mechanism largely enclosed within the handle, without the need for tools and risk of losing parts during assembly or disassembly. The only externally visible part of the screw mechanism is the thumbwheel, and it extends only slightly from the major flat surfaces of the handle, making the tool free of protuberances that might interfere with the intended use of the tool and giving it a neat appearance.

Figure 8:
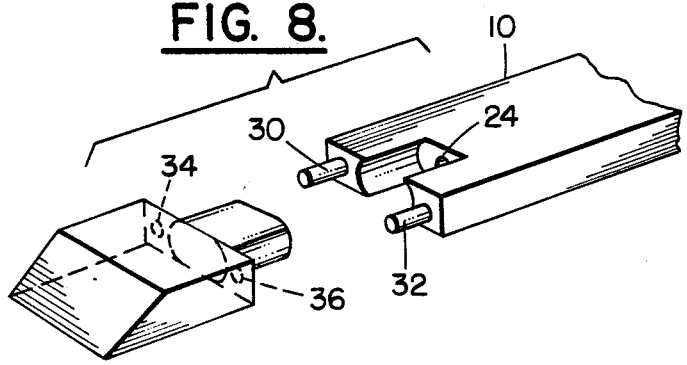
FIG. 8 is a fragmentary, exploded, perspective view of an alternative construction of the tool.

While in most cases the relative widths of the handle 10 and the shank portion 26 of the tool piece are such that the handle extensions defining the cutout have sufficient strength and rigidity to resist any tendency of the tool piece to rotate with respect to the handle when subjected to rotational forces in use, if a modular tool system having a narrower handle should be desired it may be necessary, in view of the reduced cross-sectional area of the extensions, to provide additional means for insuring against relative rotation of tool piece and handle. This is accomplished in the alternative construction illustrated in FIG. 8 by a pair of pins 30 and 32 projecting longitudinally from the cutout-defining projections of the handle, parallel to the axial bore 24, and received in a pair of openings 34 and 36 formed in the transverse surface 28 of an assembled tool piece. The pins may be press-fit in openings formed in the handle, and the openings 34 and 36 are slightly larger than the pins so as to receive them with a tight sliding fit.

It now should be apparent that the present invention provides an improved modular hand tool system comprising a relatively simple mechanical assembly of a planar handle member having a contoured cutout at one end for receiving a similarly-contoured shank portion of a tool piece, and a screw mechanism largely contained within the handle for detachably securing the handle and tool piece together. Although an exemplary embodiment of the inventive modular tool system is illustrated and described, it will be understood that the disclosed embodiment may be subjected to changes, modifications and substitutions without necessarily departing from the spirit of the invention. For example, the matching contours of the cutout and shank may have a shape other than semicircular, so long as it prevents relative rotation between the tool piece and handle.

I claim:

1. A modular hand tool system comprising:
   an elongated planar handle member having width and thickness and at one end having a first cutout of selected length and width extending therethrough equidistant from the edges, the longitudinally extending surfaces of which are contoured, said handle member further having a second cutout extending therethrough equidistant from the edges and spaced from said first cutout, and an axial bore extending from an inner transverse edge of said first cutout to said second cutout;
   one or more tool pieces each comprising a cutting portion having a transverse surface of substantially the same width and thickness as said handle member and a shank portion integrally joined to said transverse surface equidistant from the edges thereof, said shank portion having substantially the same dimensions as said first cutout and being contoured to match the longitudinally extending contoured surfaces of said first cutout so as to be received therein with a tight sliding fit, said shank portion having a threaded hole extending longitudinally inward from the free end thereof; and
   means for detachably securing a selected tool piece to said handle member comprising an elongated rod supported for rotation in the axial bore in said handle member, said rod being anchored at one end to said handle member at said second cutout and at its other end threadably engaging the threaded hole in the shank portion of a tool piece inserted in said first cutout and which when rotated in one direction draws said shank portion into said first cutout for securing it therein, and when rotated in the opposite direction pushes said shank portion out of said first cutout and releases the tool piece from the handle member.

2. A modular hand tool system as defined by claim 1, wherein said one end of said elongated rod is anchored to said handle member at said second cutout by a thumbwheel threadably engaging said one end of said elongated rod and releasably secured to a longitudinally adjusted position thereon, said thumbwheel having a diameter sufficiently greater than the thickness of said handle member that it projects from the major surfaces of the handle member by an extent to be finger-manipulable.

3. A modular hand tool system as defined by claim 2, wherein said second cutout is spaced from said first cutout sufficiently that said thumbwheel does not interfere with the use of the tool piece.

4. A modular hand tool system as defined by claim 1, wherein the contoured surfaces of said first cutout and of the shank portion of said tool piece are substantially semicircular arcs having diameters substantially equal to the thickness of said handle member.

5. A modular hand tool system in which any of a multiplicity of tool pieces may be detachably secured to a handle, said system comprising:
   an elongated planar handle member having width and thickness and at one end having a first rectangular-shaped cutout therethrough extending inwardly a selected distance, the longitudinally extending surfaces of which have a curved contour, said handle member further having a second rectangular-shaped cutout therethrough spaced from said first cutout, and an axial bore extending between said first and second cutouts;
   a tool piece having a cutting portion having a transverse surface of substantially the same width and thickness as said handle member and a rectangular-shaped shank portion having substantially the same dimensions as said first cutout and curved side edges matching the contoured surfaces of said first cutout integrally and centrally joined to said transverse surface and extending longitudinally therefrom and adapted to be received with a tight sliding fit in said first cutout, said shank portion having a threaded opening extending axially inwardly from the free end thereof; and
   a screw mechanism for detachably securing a selected tool piece to said handle member comprising an elongated rod supported for rotation in the axial bore in said handle member and anchored at one end to said handle member at said second cutout and at its other end threadably engaging the threaded axial opening in the shank portion of a tool piece inserted in said first cutout, which when rotated in one direction draws the shank portion of a tool piece into said first cutout for securing it therein and when rotated in the opposite direction forces the shank portion out of said first cutout and releases the tool piece.

6. A modular hand tool system as defined by claim 5, wherein the matching curved contours of said first cutout and of said shank portion are substantially semicircular arcs having diameters substantially equal to the thickness of said handle member, and
   wherein said one end of said rod is anchored to said handle member by a finger-manipulable thumbwheel disposed within said second cutout and secured at a longitudinally adjusted position along said rod at which the other end of the rod projects a desired distance from the transverse surface of said first cutout.

* * * * *